United States Patent
Amaldi et al.

(10) Patent No.: US 8,405,056 B2
(45) Date of Patent: Mar. 26, 2013

(54) ION ACCELERATION SYSTEM FOR MEDICAL AND/OR OTHER APPLICATIONS

(75) Inventors: Ugo Amaldi, Cologny (CH); Saverio Braccini, Arezzo (IT); Giulio Magrin, Ferney Voltaire (FR); Peter Pearce, Prevessin Moens (FR); Riccardo Zennaro, Versoix (CH)

(73) Assignee: Fondazione per Adroterapia Oncologica—TERA, Novara (IT)

( * ) Notice: Subject to any disclaimer, the term of this patent is extended or adjusted under 35 U.S.C. 154(b) by 321 days.

(21) Appl. No.: 12/521,724

(22) PCT Filed: Dec. 28, 2006

(86) PCT No.: PCT/IT2006/000879
§ 371 (c)(1),
(2), (4) Date: Sep. 10, 2010

(87) PCT Pub. No.: WO2008/081480
PCT Pub. Date: Jul. 10, 2008

(65) Prior Publication Data
US 2010/0320403 A1      Dec. 23, 2010

(51) Int. Cl.
*A61N 5/01* (2006.01)
*H05H 9/00* (2006.01)
*G21G 5/00* (2006.01)

(52) U.S. Cl. ............. 250/505.1; 250/396 R; 250/423 R; 250/424; 250/492.3; 315/500; 315/502; 315/505; 376/157

(58) Field of Classification Search .................. None
See application file for complete search history.

(56) References Cited

U.S. PATENT DOCUMENTS

| | | | |
|---|---|---|---|
| 4,641,104 A | | 2/1987 | Blosser et al. |
| 5,382,914 A | * | 1/1995 | Hamm et al. .................. 315/505 |
| 5,619,042 A | * | 4/1997 | Hughes ...................... 250/492.3 |
| 5,635,721 A | | 6/1997 | Bardi et al. |
| 5,976,066 A | * | 11/1999 | Yanch et al. ....................... 600/1 |
| 6,011,825 A | * | 1/2000 | Welch et al. .................. 376/195 |
| 6,580,084 B1 | * | 6/2003 | Hiramoto et al. .......... 250/505.1 |
| 2004/0108823 A1 | * | 6/2004 | Amaldi et al. ................. 315/505 |

FOREIGN PATENT DOCUMENTS

CA     10425521 A1     11/1978
(Continued)

OTHER PUBLICATIONS

XP002448137, Amaldi et al., "The RITA Network and the Design of Compact Proton Accelerators", ISBN 88-86409-08-7, Aug. 1996, Frascati (Roma) Italy, p. 217, p. 220, p. 221, and p. 250.

*Primary Examiner* — Johannes P Mondt
(74) *Attorney, Agent, or Firm* — Young & Thompson

(57) ABSTRACT

The ion acceleration system or complex (T) for medical and/or other applications is composed in essence by an ion source (1), a pre-accelerator (3) and one or more linear accelerators or linacs (6, 8, 10, 13), at least one of which is mounted on a rotating mechanical gantry-like structure (17). The isocentrical gantry (17) is equipped with a beam delivery system, which can be either 'active' or 'passive', for medical and/or other applications. The ion source (1) and the pre-accelerator (3) can be either installed on the floor, which is connected with the gantry basement, or mounted, fully or partially, on the rotating mechanical structure (17). The output beam can vary in energy and intensity pulse-by-pulse by adjusting the radio-frequency field in the accelerating modules of the linac(s) and the beam parameters at the input of the linear accelerators.

17 Claims, 5 Drawing Sheets

FOREIGN PATENT DOCUMENTS

| EP | 0940158 | A1 | 9/1999 |
|----|---------|----|--------|
| FR | 2253340 | A1 | 6/1975 |
| RU | 2147900 | C1 | 4/2000 |
| WO | 2006081847 | A1 | 8/2006 |

* cited by examiner

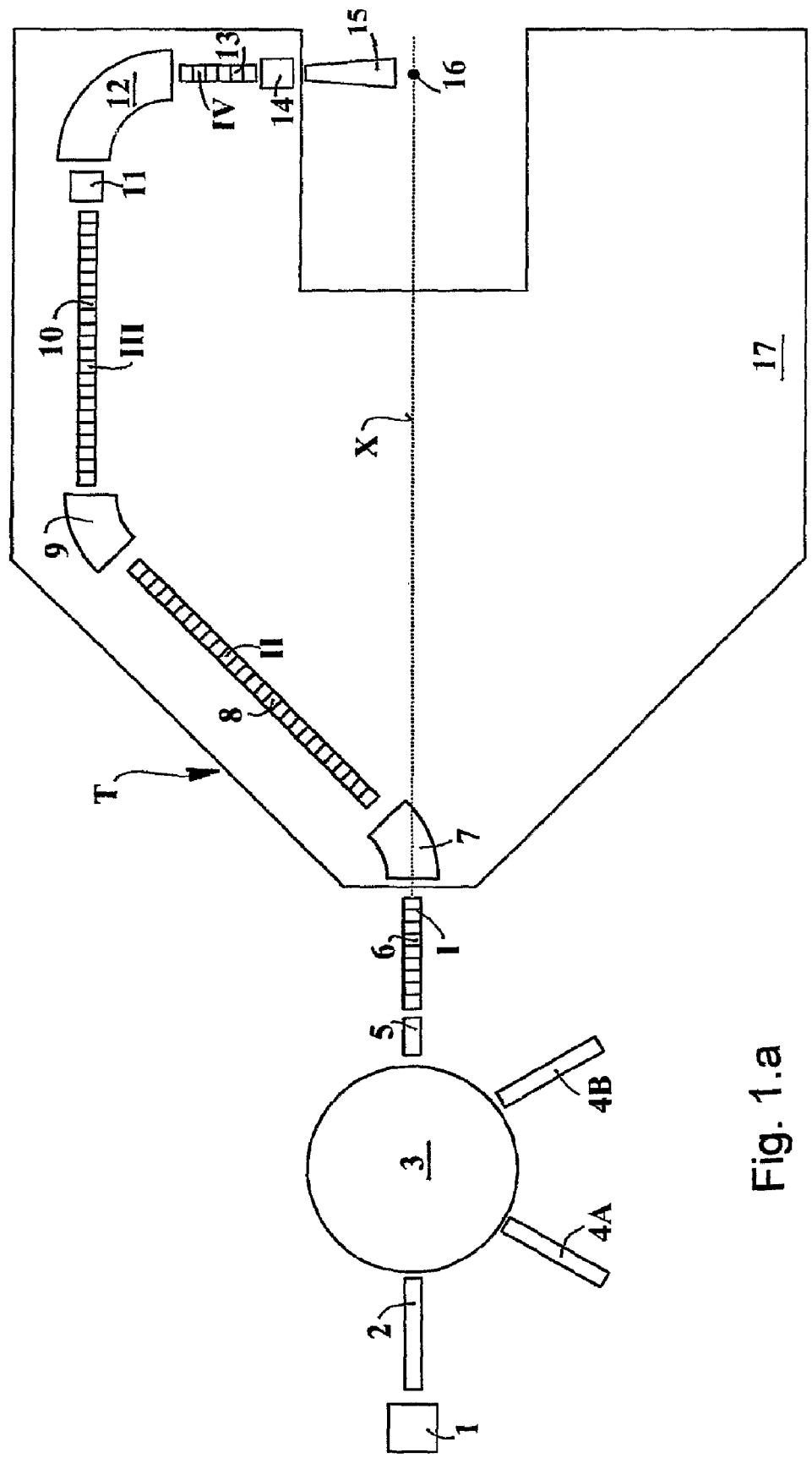
Fig. 1.a

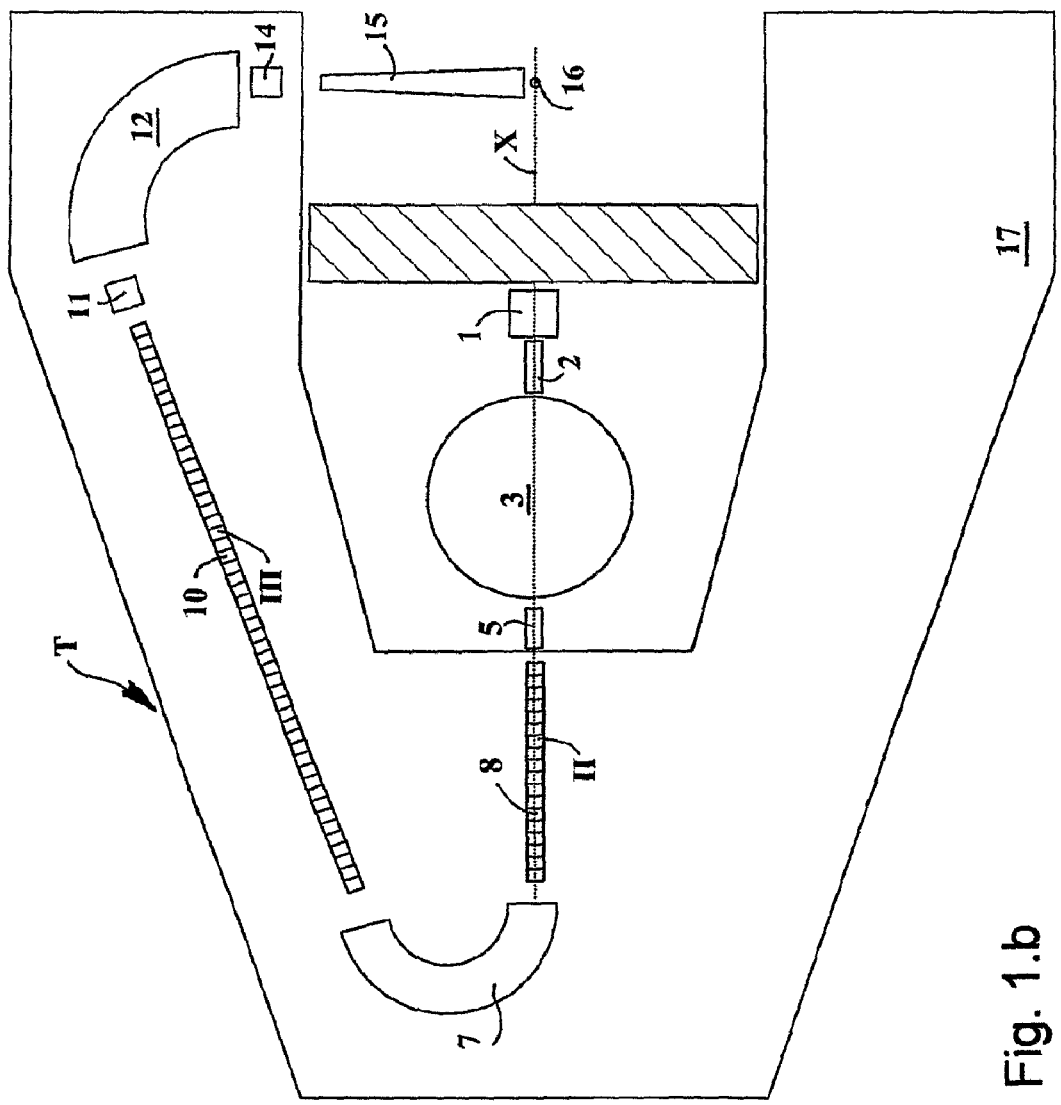
Fig. 1.b

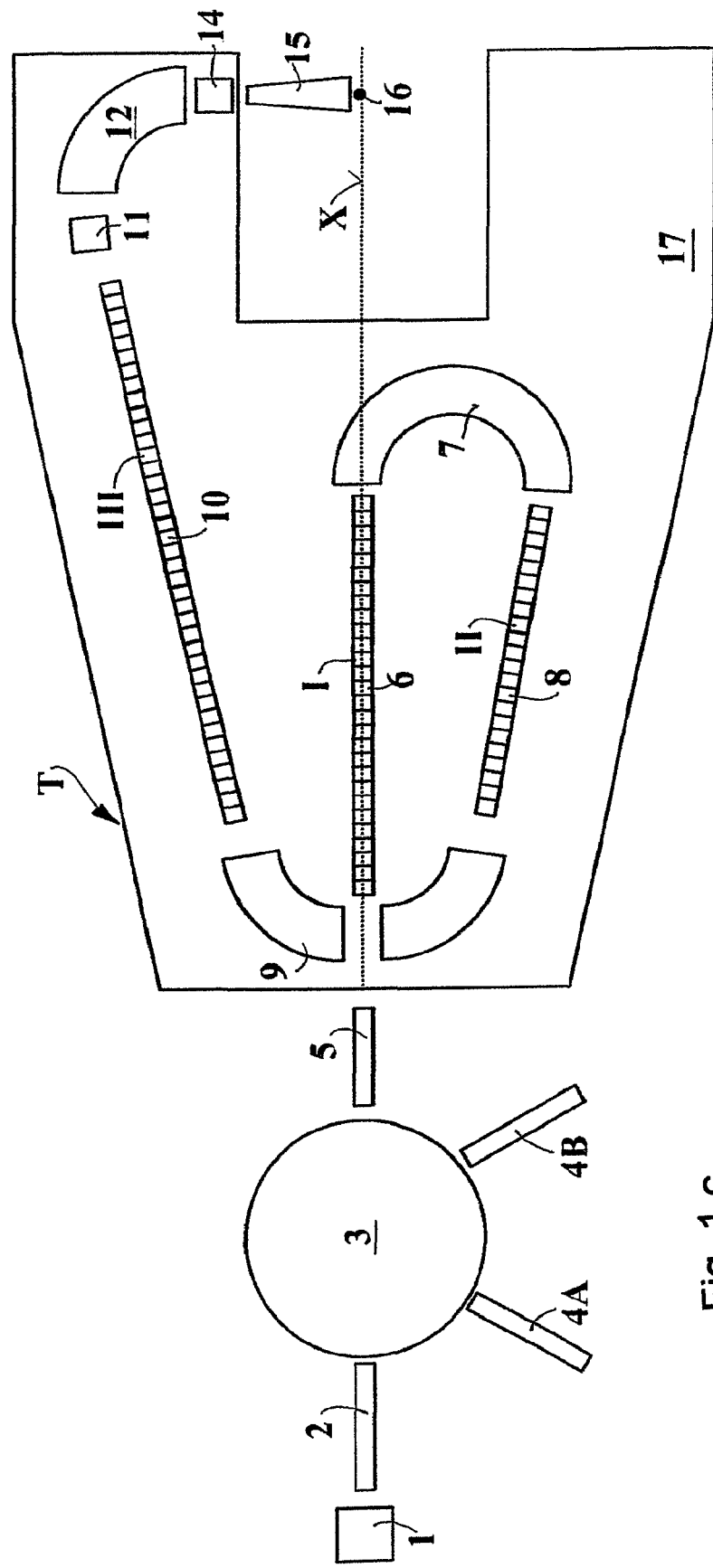
Fig. 1.c

ION ACCELERATION SYSTEM FOR MEDICAL AND/OR OTHER APPLICATIONS

FIELD OF THE INVENTION

The present invention relates to a complex or system of particle accelerators, which includes one or more linear accelerators (linacs) according to the preamble of claim 1.

BACKGROUND OF THE INVENTION

It is known that hadron therapy is the modern cancer teletherapy that uses beams either of protons or of heavier nuclear charged particles with mass number larger than 1.

It is equally known that in protontherapy, which is a particular hadron therapy technique based on the use of proton beams, therapeutic beams of relatively low current (of the order of some nanoamperes) are used, with energies in the range 60 to 250 MeV.

It is also known that, in the case of different ion species, therapeutic beams with lower currents and higher energies are required compared to the ones for the protons. For example, in the case of carbon ions $^{12}C^{6+}$, the required energies are between 1.500 and 5.000 MeV (i.e. 120 and 450 MeV/u) and currents of a fraction of nanoampere.

In this field of teletherapy different types of accelerators are used: cyclotrons (isochronous or synchrocyclotrons; conventional or superconducting) or synchrotrons.

Recently Fixed Field Alternating Gradient (FFAG) accelerators have also been considered.

Linear accelerators (linacs) have been proposed by the Requestor for both proton and light ion therapy. 1) U.S. Pat. No. 6,888,326 B2 "Linac for Ion Beam Acceleration, U. Amaldi, M. Crescenti, R. Zennaro. 2) U.S. patent application Ser. No. 11/232,929 "Ion Accelerator System for Hadrontherapy, Inventors: U. Amaldi, M. Crescenti, R. Zennaro, filed on 23, Sep. 2005. 3) "Proton Accelerator Complex for Radioisotopes and Therapy, U. Amaldi, filed on 24. Apr. 2006.

Several companies offer turn-key centres for proton and/or carbon ion therapy. Typically a centre for more than 400-500 patients/year is located in a large multi-floor building, specially made to host the high-tech apparata, offices and services for the personnel and the reception of the patients for a total surface of many thousands square metres. It features a hadron accelerator (cyclotron, synchrocyclotron, synchrotron, linac or a combination of these) and a system of magnetic beam transport channels to irradiate solid tumours with 2-4 gantries, which rotate around the patient, and one or more horizontal therapeutic beams. A complete multi-room centre with its infrastructures requires an investment that is in the range 60-130 million Euro, the larger figure corresponding to a 'dual' carbon ion and proton multi-room facility.

Hadron therapy has a large potentiality of further developments, as indicated by the epidemiological studies performed in Austria, France, Italy and Germany, that have been reported, for example, in "Carbon ion therapy, Proceedings of the HPCBM and ENLIGHT meetings held in Baden (September 2002) and in Lyon (October 2003)" [Radiotherapy and Oncology 73/2 (2004) 1-217]. However these potentialities are hindered by the necessity of large capital investments to construct multi-room facilities. The potentialities can be summarized by recalling that the quoted studies reach the conclusion that in the medium-long term about 12% (3%) of the patients treated today with 'conventional' radiotherapy (i.e. with high-energy photons) would be better cured and/or have less secondary effects if they could be irradiated with proton (carbon ion) beams.

Only 1-2% of the 12% tumour indications for proton therapy are accepted by most radiation oncologists. The other 10% of the patients is not considered today as carrying elective indications for proton therapy by many specialists. This in spite of the fact that they would certainly profit from this irradiation modality, since the tumours are close to critical organs and it is proven that a 10% increase in the dose—for the same irradiation of critical organs—implies a 15-20% increase of the Tumour Control Probability (TCP). However it is sure that, with the accumulation of clinical trials, the first fraction of the patients will increase and the second one decrease.

For ion therapy, which is a qualitatively different type of radiation (because in each traversed cellular nucleus a carbon ion leaves 20 times more energy than a proton having the same range) further clinical studies are needed. It is in fact necessary to confirm that on 'radioresistant' tumours ions are more effective than photons and protons and that it is clinically safe to reduce the number of treatment sessions (ipofractionation). From other points of view such an approach is certainly advantageous since it implies a reduction of the costs and of the psychological burden to the patient.

Starting from these figures—and taking into account that in a population of 10 million and in a year about 20,000 patients are irradiated with photons—the number of hadron therapy treatment rooms needed within five/ten years are shown in the table. Two simplifying hypotheses have been made on the basis of clinical experience: (1) the number of sessions per patients scales as 1:2:3 for ions, protons and photons, respectively and (2) a photon (hadron) session lasts 15 min (20 min).

| Radiation treatment | Pts. per year in $10^7$ people | Average No. of sessions per patient | Sessions per day (12 h) in one room | Pts per year (230 d) in one room | Rooms per 10 million people | Rooms per 10 million people Factor ≈ |
|---|---|---|---|---|---|---|
| Photons | 20 $10^3$ | 30 | 48 | 370 | 54 | $8^2$ |
| Protons (12%) | 2.4 $10^3$ | 20 | 36 | 410 | 5.8 | 8 |
| C ions (3%) | 0.6 $10^3$ | 10 | 36 | 830 | 0.7 | 1 |

The estimated numbers of rooms come out to be in the easy to remember "rule of thumb" $1:8:8^2$.

Since a typical hadron therapy centre has 3-4 rooms, the figures of the table say that a proton (carbon ion) centre would be needed for about every 5 (40) million people. If the carbon centre is 'dual' and patients are treated also with protons, the number of inhabitants who can be served decreases from 40 to about 30 millions.

These arguments indicate that the development of hadron therapy requires a change with respect to the presently dominating 'paradigm', which sees a multi-floor building serving 5 million people (or many more in the carbon ion case) because it features one accelerator and 3-4 gantries. In the long term, a more flexible and patient-friendly paradigm will most probably dominate being based on a single-room accelerator/gantry system for either protons or light ions (carbon), which is constructed on a relatively small area (about 500 m$^2$).

At present, small or large radiotherapy departments run 1-2 or 5-6 electron linacs respectively so that, on average, 8 conventional rooms are present in 3-4 hospitals covering a population of 1.5-2 millions. To maintain the proportions appearing in the last column of the table, two uses of such single-room facilities can be envisaged:

a single-room proton facility is "attached" to one of these hospitals but also serves 2-3 others;

a single-room carbon linac facility is "attached" to an already existing proton therapy centre which serves many million inhabitants but accelerates carbon, and possibly other light ions, to an energy which is not sufficient to treat deep seated tumours.

Proton accelerators which are mounted on a gantry rotating around an axis, and thus the patient, have been considered previously. In the 80's a rotating 60 MeV superconducting cyclotron for neutron therapy was constructed by H. Blosser and collaborators for built for the Harper Hospital (U.S. Pat. No. 4,641,104). Following this realization, more than fifteen years ago a 250 MeV superconducting cyclotron for proton therapy was proposed (H. Blosser et al, *Medical accelerator projects at Michigan State University*, Proc. 1989 Particle Acceleration Conference, IEEE, 1989, 742-746). Recently the construction project of a single room apparatus based on a rotating synchrocyclotron has been announced (http://web.mit.edu/newsoffice/2006/proton.html, press release of MIT, 28 Aug. 2006).

SUMMARY OF THE INVENTION

The basic aim of the present invention is to propose facilities for hadron therapy based on a high frequency linac (or more than one linac section) which is (are) mounted on a rotating gantry and used for the irradiation from more than one direction of a patient.

This aim is reached by a system or complex of ion accelerators with the features of claim 1. Further developments are inferable from the dependent claims.

To answer the needs described above, according to the present invention, protons and/or ions are accelerated to the energy needed for therapy (or for any other application) by one or more high-frequency linac section(s). At least one of these sections is mounted on a gantry which can rotate around the target so that the optimal beam direction can be chosen. The injector of the moving linac (named here "pre-accelerator") can be either a circular accelerator (cyclotron, synchrocyclotron, FFAG or other) or a low-velocity linac or a combination of two or more of these well known accelerators.

Moreover the ion beams produced by some of the components of the pre-accelerator can be used for other purposes, for instance to treat patients or/and to produce radioisotopes for medical purposes or/and for industrial applications. Typically the pre-accelerator is rigidly fixed on the floor supporting the rotating gantry, but it can also be, in part or fully, mounted on the gantry.

In cancer therapy a linac mounted on a gantry rotating around the patient is a solution which is simpler, more flexible and surer than the ones based on circular accelerators mounted on gantries. Indeed the output beam is pulsed with rates in the range 50-500 Hz and can be very easily coupled to an 'active' dose spreading system, since the particle energy and the dose given to a voxel can be adjusted, electronically and in about 1 millisecond, from pulse to pulse (R. Zennaro, *IDRA: Design Study of a Proton Therapy Facility*, Beam Dynamics Newsletter, n. 36, p. 62, April 2005). This unique property implies that there is no need for absorbers to reduce the beam energy, as in fixed-energy cyclotrons. As a consequence the unwanted production of intense and difficult to shield neutron fluxes close to the patient is avoided.

A high-frequency linac is superior to the all other types of accelerator because the beam energy can be varied from pulse to pulse together with the number of particles do be delivered to the tumour target. The time and intensity structure of the pulsed beam are particularly suited for doses delivered in an 'active' way, for instance implementing either the techniques of 'spot scanning', as in use at the PSI Centre, Paul Scherrer Institute, Villigen, Switzerland (E. Pedroni et al, *The 200 MeV proton therapy project at the Paul Scherrer Institute: conceptual design and practical realisation*, Medical Physics, 22(1), (1995) 37), or of 'raster scanning', as in use at the GSI Centre, Darmstadt, Germany (Th. Haberer, et al, *Magnetic scanning system for heavy ion therapy*, Nuclear Instruments and Methods A 330 (1993) 296). As mentioned above, further favorable developments of the invention are pointed out in the dependent claims.

The use of the ion acceleration system for hadron therapy according to the invention presents many important advantages. First of all the accelerator is lighter with respect to existing cyclotrons and synchrotrons, and is characterized by a modular structure composed of the same high technology equipment repeated almost without variation for each accelerating module. Secondly, the proposed system is relatively compact, so minimal volumes and installation surfaces are needed, therefore facilitating the installation in hospital centers. Moreover, the high frequency of the linac allows for a reduction in power consumption which reflects in reduced exploitation costs.

In summary, with respect to the hadron therapy facility either in use or conceived, the present invention allows 1) to build compact facilities 2) having a single-room which 3) can be installed also in already existing medium sized hospitals leading so 4) to lead, due to the relatively low cost, to a wide spread diffusion of tumour hadron therapy.

The disclosed system is dubbed TULIP for "TUrning LInac for Particle therapy".

The linacs, disclosed in the documents WO 2004/054331 and U.S. Pat. No. 6,888,326 B2 in the name of the Applicant, can be used as the high frequency modular linacs which can be used for the present invention. Their content is hereby included for reference.

BRIEF DESCRIPTION OF THE DRAWINGS

Further advantages, details and characteristics of the ion acceleration system for hadron therapy according to the invention will furthermore result from the following description of examples of preferred embodiments of the invention, schematically illustrated in the annexed drawings, in which:

FIGS. 1.*a*, 1.*b*, 1.*c*, 2 and 3 show block diagrams of various possible embodiments of a ion acceleration system or complex for hadrontherapy according to the invention.

DETAILED DESCRIPTION OF THE PREFERRED EMBODIMENTS

Figure 2:
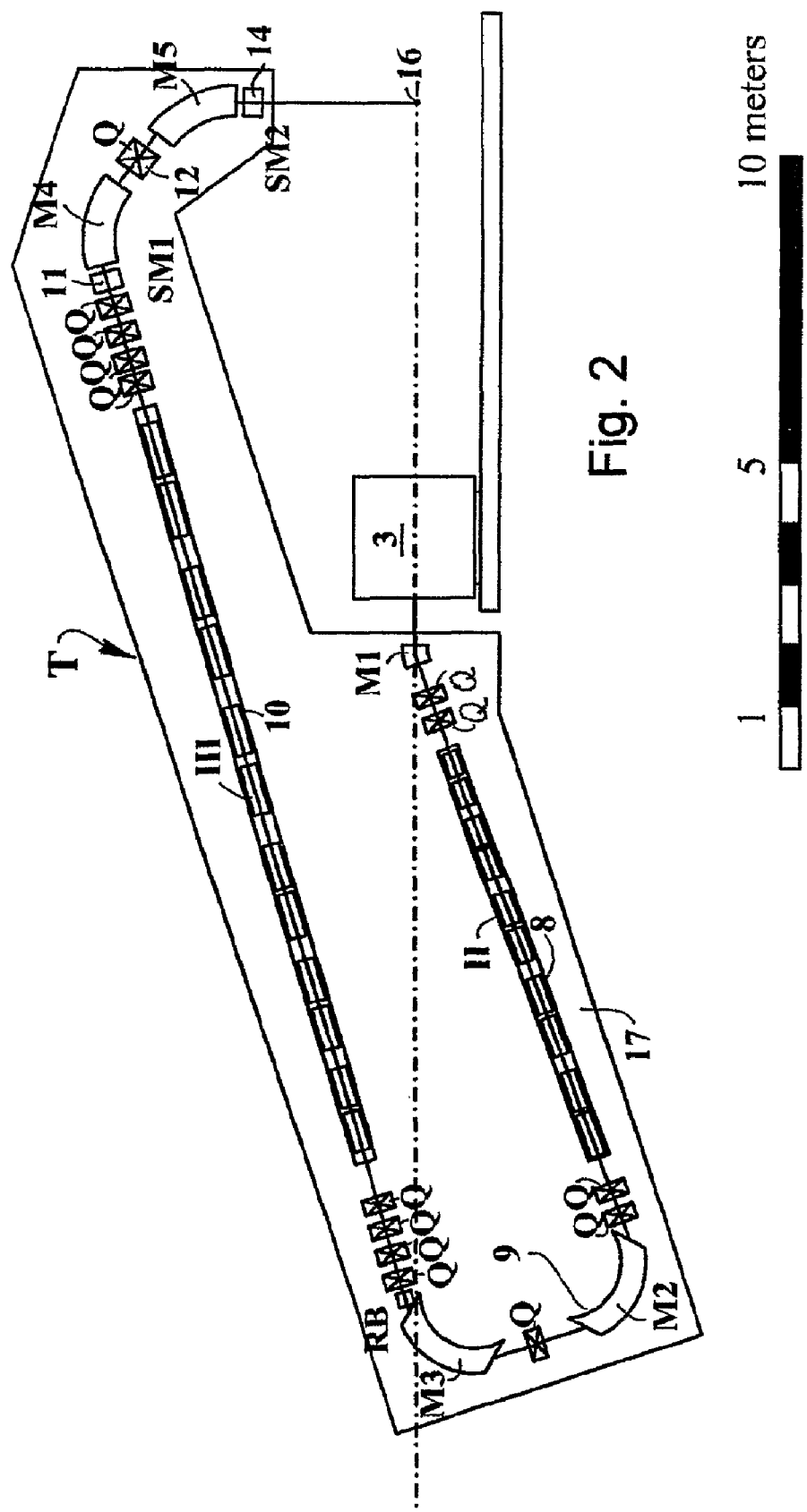

The components of the complexes T of hadron accelerators shown in FIG. 1.*a*, 1.*b*, and 1.*c* are the following:

1. ion source;
2. Low Energy Beam Transport channel (LEBT);
3. cyclotron (normal or superconducting) or FFAG (normal or superconducting) or other circular accelerator;
4. 4A and 4B: beams extracted from the circular accelerator 3 and used for other purposes either in parallel or alternatively with the gantry;
5. Medium Energy Beam Transport channel (MEBT);
6. first (I) linac section, at a frequency typically greater than 1 GHz, and beam transport magnetic channel;
7. first Integrated Magnetic Transport Channel ($1^{st}$ IMTC) made of quadrupoles, bending magnet(s) and RF buncher(s) to transport, bend and shape the hadron beam;
8. second (II) linac section with a frequency that can be a multiple of the one of the first linac section (I);
9. second Integrated Magnetic Transport Channel ($2^{nd}$ IMCT) made of quadrupoles, bending magnet(s) and RF buncher(s) to transport, bend and shape the hadron beam;
10. third (III) linac section with a frequency that can be a multiple of the one of the second linac section;
11. scanning magnet(s), placed either upstream or at the centre or downstream of item 12, to move transversally the hadron beam for an 'active' delivery of the dose;
12. third Integrated Magnetic Transport Channel ($3^{rd}$ IMCT) made of quadrupoles, large angle bending magnet(s) and RF buncher(s) to transport, bend and shape the hadron beam;
13. fourth (IV) linac section with a frequency that can be a multiple of the one of the third linac section;
14. in the case of 'active' delivery, scanning magnet(s) to move transversally the hadron beam or, in the case of 'passive' delivery, system of scatterer(s), absorber(s), filter(s) and collimator(s);
15. monitoring system of the therapeutic beam.
16. focus of the dose delivery system;
17. metallic structure (gantry) partially or fully rotating around an axis X and rigidly supporting the components 7-15.

Referring to the more general FIG. 1.a, according to the invention the hadron accelerator complex T includes in principle various kinds of accelerators serially connected, namely a circular accelerator 3 (which can be can be either at room temperature or superconducting) and a number of linac sections (6, 8, 10, 13), possibly of increasing frequencies so to have in the latter stages a higher gradient and thus reduce the overall dimensions of the system. To simplify the overall scheme some of the four linac sections may be absent and/or may be placed in a topologically different set-up, as shown for instance in FIGS. 1.b and 1.c.

Each linac section is made of accelerating modules which can have structures of the Drift Tube Linac (DTL) or Cell Coupled Linac (CCL) type according to the speed of the accelerated hadrons. Two of these structures are disclosed in the documents WO 2004/054331 and U.S. Pat. No. 6,888,326 B2 in the name of the Applicant and are here quoted and incorporated as a reference so that it is not necessary to further provide details on the structures of the accelerating modules.

It has to be remarked that the output energy of the circular accelerator 3 is usually fixed and therefore its value is chosen according to the desired application and, more precisely, according to the type of centre that one wants to develop and/or the use one possibly wants to make of other extracted beams, exemplified by 4A and 4B in FIGS. 1.a and 1.c. The circular accelerator is fed by either an internal or external source 1 via, usually, a low energy beam transport line 2. Its output beam can be continuous or modulated at the repetition frequency of the linac(s).

A beam at the exit of the circular accelerator 3 is transported to the gantry system by a magnetic channel made of bending magnets and quadrupoles and a linac section 6. The rest of the system is mounted on the gantry 17. In some embodiments the circular accelerator 3 is not needed and the linac 6 with its transport channel pre-accelerates the hadrons both for the uses exemplified by 4A and 4B and for the injection in the $1^{st}$ IMTC 7. In other embodiments the circular accelerator is rigidly connected with the gantry, as indicated in FIG. 1.b.

The subsystems supported by the gantry and drawn in the FIGS. 1.a, 1.b and 1.c are not necessarily all present in a single embodiment. In general the linac section producing the largest acceleration gradient is the one indicated as 10 in the FIGS. 1.a, 1.b and 1.c.

The third Integrated Magnetic Transport Channel ($3^{rd}$ IMCT) 12 directs the focused particle beam to the patient and is an essential component of the overall system. It is made of well known components (normal or superconducting) as quadrupoles and large angle bending magnet(s). In some embodiments it can be followed by linac section 13 of FIG. 1.a. The two scanning magnets 11 and/or 14 move the beam transversally either in a divergent or in a parallel configuration. They can be placed before, in the middle or after the $3^{rd}$ IMCT. These magnets when an 'active' delivery system is used, define the dimensions of the irradiated field. In case of a 'passive' scattering the scanning magnets 11 and 14 are not needed and the particles are spread out, moderated in energy and collimated by well know components: scatterers, absorbers, filters, collimators etc.

In the illustrated Figures the sources of the RF power are not shown. They are typically high-frequency klystrons running at repetition rates larger than 50 Hz. These devices can be either mounted on the gantry 17 or are located outside the gantry and connected to the modules of the Linac via rotating wave-guide devices. These can be commercial rotating radiofrequency power devices or consist of two rotating and closely coupled mode converters facing one another and separated by a small gap. This invention differs from the development done at SLAC on 11.4 GHz non-rotating mode converters (V. A. Dolgashev et al, *Design of Compact Multi-Megawatt Mode Converter*, Slac-Pub-11782), which has been subsequently scaled down for 3 GHz operation at the CERN CLIC test facility (A. Grudiev, *Development of a Novel RF Waveguide Vacuum Valve*, EPAC 06, Edinburgh, UK, June 2006).

In the following, to complete the general description of the TULIP complex, two embodiments are given according to the invention.

In the first one protons are accelerated to 230 MeV adopting the scheme of FIG. 2. The protons produced by the source 1 are gated at 200 Hz and injected by the LEBT 2 in a 24 MeV cyclotron 3. Only the II and III linac sections (8 and 10) are present. They are both of the SCL Side Coupled Linac) type and are mounted on the gantry 17. They may be powered by commercial radiofrequency amplifiers (klystron), as for example those produced by the company Thales Electron Devices (78941 Velizy, France) or CPI (Palo Alto, Calif. 94303-0750, USA).

For the transverse beam focusing, both linacs use very small commercial quadrupole permanent magnets (QPM), such that they can fit between two consecutive accelerating sections, forming an alternate focusing, FODO type system.

In between linac 8 and linac 10 the Integrated Magnetic Transport Channel 9 ($2^{nd}$ IMTC) is made of seven quadrupoles, Q, and two bending magnets (M2 together with M3) and contains a four-gap RF buncher, RB, to re-bunch longitudinally the beam which becomes continuous in the long drift between linac 8 and linac 10. The bending magnets for the transverse scanning, SM1 and SM2, are one upstream, 11, and the other downstream, 14, of the third Integrated Magnetic Transport Channel 12 (3$^{rd}$ IMCT made of M4 together with M5 and the quadrupoles Q) so that the average distance between the virtual focus of the therapeutic beam and the focal point 16 is about 3.5 metres. The irradiation field is 20×20 cm$^2$. A dose of 2 grays can be delivered to a 1 liter tumour by painting it about 20 times with the spot scanning technique in a couple of minutes. This technique is optimal for the irradiation of moving organs.

The main parameters of the embodiment shown in FIG. 2 are summarized in Table 1.

TABLE 1

Basic parameters of the embodiment of FIG. 2.

| General features | |
| --- | --- |
| Total weight [tons] | 80 |
| Total length [m] | 25 |
| Approximate radius of the gantry system [m] | 5.5 |
| Total power [kW] | 500 |
| Magnets | |
| Dipole M1: angle [deg], radius of curvature [m] | 20, 0.8 |
| Dipoles M2, M3: angle [deg], radius of curvature [m] | 92, 1.1 |
| Dipoles M4, M5: angle [deg], radius of curvature [m] | 53, 1.5 |
| Number of quadrupole magnets, Q | 14 |
| Linac 8, II | |
| Frequency [MHz] | 2998 |
| Length [m] | 7.1 |
| Number of modules | 10 |
| Repetition rate [Hz] | 200 |
| Input Energy [MeV] | 24 |
| Output Energy [MeV] | 92 |
| Duty Factor of the proton pulse at 200 Hz [%] | 0.10 |
| Linac 10, III | |
| Frequency [MHz] | 2998 |
| Length [m] | 12.8 |
| Number of modules | 12 |
| Repetition rate [Hz] | 200 |
| Input Energy [MeV] | 92 |
| Output Energy [MeV] | 230 |
| Duty Factor of the proton pulse at 200 Hz [%] | 0.10 |
| Re-buncher, RB | |
| Frequency [MHz] | 2998 |
| Number of gaps | 4 |
| Scanning Magnets | |
| SM1, 11: maximum angle [mrad], dist. virtual focus to isocenter [m] | 16, 4.2 |
| SM2, 14: maximum angle [mrad], dist. virtual focus to isocenter [m] | 37, 2.7 |
| Field at isocenter [cm × cm] | 20 × 20 |

The acceptance of the linac system is such that a cyclotron current of 15 µA is needed to obtain a maximum number of 2 10$^7$ protons/pulse, corresponding at 200 Hz to a current of 0.6 nA. The cyclotron can easily deliver a current 10 times larger but less than 1 nA is sufficient for the multi-painting of 1 liter volume and a dose delivery rate of 1 Gy/min.

Figure 3:
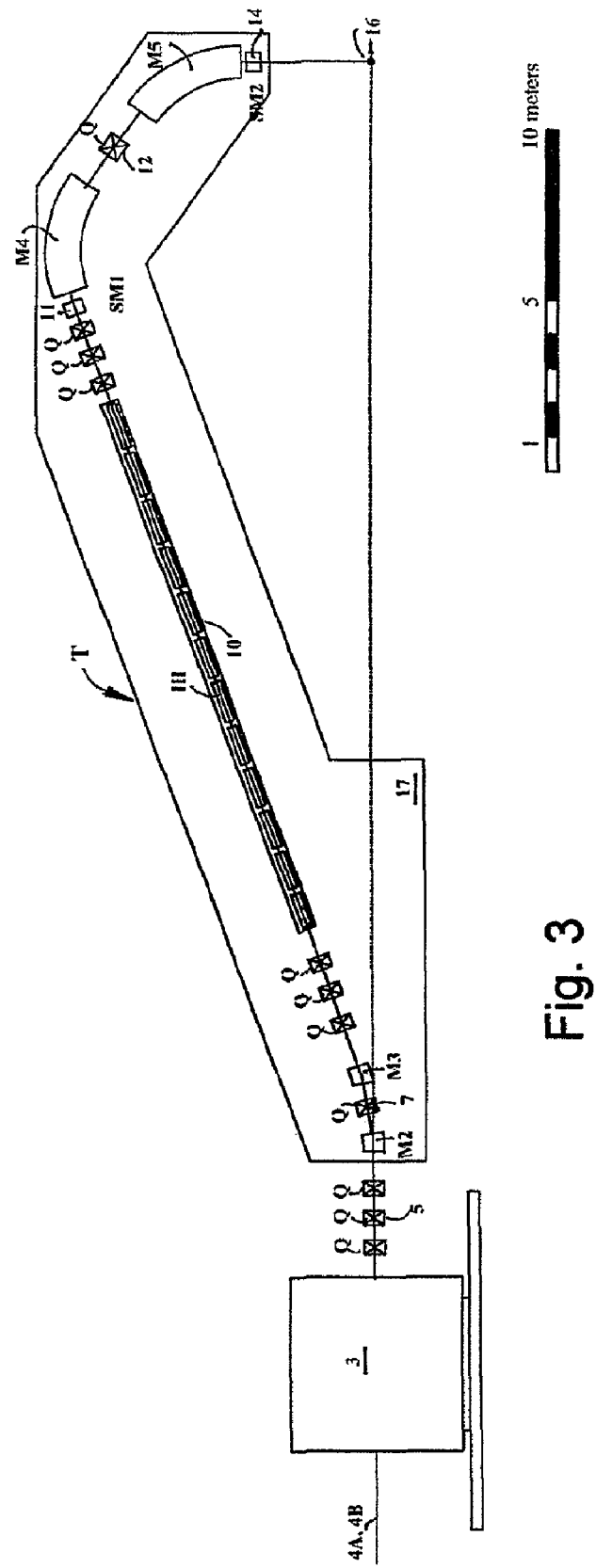

In the embodiment shown in FIG. 3 the circular accelerator is the superconducting 300 MeV/u C$^{6+}$ carbon ion cyclotron proposed by INFN—the Italian National Institute for Nuclear Physics (L. Calabretta et al, *A novel superconducting cyclotron for therapy and radioisotope production*, Nuclear Instruments and Methods A562 (2006) 1009-1012) and commercialized by the company IBA—Ion Beam Application from Belgium (http://www.iba.be/documents/contribute/PR-INFN-GB.pdf—IBA press release, *Hadrontherapy: The new 300 MeV/u superconducting cyclotron developed by INFN will be commercialized by IBA*", Sep. 26, 2006).

The beams 4A and 4B of FIG. 3 are proton and carbon ion beams used for therapy of deep seated tumours with protons (water range=35 cm) and of shallow tumours with carbon ion (water range=17 cm). To treat deep seated tumours carbon ions have to have at least 400 MeV/u (27 cm range) and the present invention is particularly useful to fully exploit the potential of a 230-300 MeV/u cyclotron for carbon ion therapy.

The magnetic rigidity of these carbon ions is about 2.5 times larger than the one of 250 MeV protons, so that the dimensions and weights of the second embodiment of the invention are definitely larger than the ones of the first. But this is not a too serious inconvenience since ordinary gantries for carbon ions are already very large, weighty and costly: the only known example is the one built for the HIT centre in Heidelberg which is 25 meter long, has a radius of 5 meters, weights 600 tons and consumes about 400 kW (R. Fuchs et al, *The heavy ion gantry of the HICAT facility*, Proceedings of EPAC 2004, Lucerne, Switzerland). The present invention allows to have (within about the same dimensions, weight and power) a booster accelerator that brings the carbon beam to 400 MeV/u and a delivery system which is fully 'active' on a 20×20 cm$^2$ field.

In this embodiment, shown in FIG. 3, the first linac section 6 fixed on the floor (FIG. 1.*a*) is not foreseen. The first Integrated Magnetic Transport Channel (1$^{st}$ IMTC) 7 is made of seven quadrupoles and two bending magnet(s) and sends the beam to the second linac section 8 which is of the CCL type as in the first embodiment. The second Integrated Magnetic Transport Channel (2$^{nd}$ IMCT) and the third linac 10 are not foreseen. The geometry of the third Integrated Magnetic Transport Channel (3$^{rd}$ IMCT) 12 and of the scanning magnet(s) 14 to move transversally the hadron beam are similar to the ones of the first embodiment, with dimensions scaled up by a factor 2.3 because of the larger magnetic rigidity of the hadrons.

The main parameters of the embodiment shown in FIG. 3 are given in Table 2.

TABLE 2

Basic parameters of the embodiment shown in FIG. 3

| General features | |
| --- | --- |
| Total weight [tons] | 500 |
| Total length [m] | 33 |
| Approximate radius of the gantry system [m] | 9.6 |
| Total power [kW] | 900 |
| Magnets | |
| Dipoles M2, M3: angle [deg], radius of curvature [m] | 10, 3.3 |
| Dipoles M4, M5: angle [deg], radius of curvature [m] | 55, 3.9 |
| Number of quadrupole magnets, Q | 11 |
| Linac 8, II | |
| Frequency [MHz] | 2998 |
| Length [m] | 16.4 |
| Number of modules | 12 |
| Repetition rate [Hz] | 400 |
| Input Energy [MeV] | 300 |
| Output Energy [MeV] | 400 |
| Duty Factor of the proton pulse at 200 Hz [%] | 0.20 |
| Scanning Magnets | |
| SM1, 11: maximum angle [mrad], dist. virtual focus to isocenter [m] | 9, 7.9 |
| SM2, 14: maximum angle [mrad], dist. virtual focus to isocenter [m] | 29, 3.5 |
| Field at isocenter [cm × cm] | 20 × 20 |

By adjusting the driving pulses of the klystrons it is possible to finely vary about every millisecond the energy of the carbon beam between 300 and 400 MeV/u, so that the water-range varies between 17 and 27 cm. To reduce the average depth it is sufficient to insert an absorber before IMTC 12.

From the structural and functional description of the various embodiments of ion acceleration complexes for hadron therapy according to the invention it should be apparent that the proposed invention efficiently achieves the stated aim and obtains the mentioned advantages. With the proposed embodiments an important reduction in dimensions may be obtained by using higher frequencies than the 2998 GHz adopted for the two described embodiments.

Those skilled in the art may introduce modifications and variations of the components and their combination, both in structure and/or dimensions, to adapt the invention to specific cases without departing from the scope of the present invention as described in the following claims.

LITERATURE

List of some publications in the sector of hadron therapy and related accelerators:
U. Amaldi and M. Silari (Eds.), "The TERA Project and the Centre for Oncological Hadrontherapy", Vol. I and Vol. II, INFN, Frascati, Italy, 1995. ISBN 88-86409-09-5. The "Blue Book".
U. Amaldi, M. Grandolfo and L. Picardi editors, "The RITA Network and the Design of Compact Proton Accelerators", INFN, Frascati, 1996, ISBN 88-86409-08-7. The "Green Book".
U. Amaldi (Ed.), "The National Centre for Oncological Hadrontherapy at Mirasole", INFN, Frascati, Italy, 1997, ISBN 88-86409-29-X. The "Red Book".
U. Amaldi et al., "A Linac-booster for Protontherapy: Construction and Tests of a Prototype", Nuclear Instruments and Methods A 521 (2004) 512-529.
L. Picardi, C. Ronsivalle and B. Spataro, "Design development of the SCDTL structure for the TOP Linac", Nuclear Instruments and Methods A, 425 (1999) 8-22.
Projet Etoile, rapport LYCEN 2002-01 (A,B,C) UCB-Lyon & DAPNIA-02-06, DSM, CEA Saclay (2002).
U. Amaldi and 5 co-authors, "Design of a Centre for Biologically Optimized Light Ion Therapy in Stockholm", Nuclear Instruments and Methods B 184 (2001) 569-588.
E. Takada et al., Proc. of the 13th Sympo. on Accel. Sci. and Tech., Osaka, Japan (2001) pp. 187-189 (HIMAC Project).
A. Itano, Proc. of the 13th Sympo. on Accel. Sci. and Tech., Osaka, Japan (2001) pp. 160-164 (HIMAC Project).
WO 2004/054331 and U.S. Ser. No. 10/602,060 "Linac for ion beam accelerator". Inventors: Ugo Amaldi, Massimo Crescenti, Riccardo Zennaro.
R. Fuchs, U. Weinrich, P. Emde, "The heavy ion gantry of the HICAT facility", Proceedings of EPAC 2004, Lucerne, Switzerland.
E. Pedroni, R. Bacher, H. Blattmann, T. Böhringer, A. Coray, A. Lomax, S. Lin, G. Munkel, S. Scheib, U. Schneider and A. Tourovsky, "The 200 MeV proton therapy project at the Paul Scherrer Institute: conceptual design and practical realisation", Medical Physics, 22(1) (1995) 37.
Th. Haberer, W. Becher, D. Schardt and G. Kraft, "Magnetic scanning system for heavy ion therapy", Nuclear Instruments and Methods A 330 (1993) 296.

The invention claimed is:

1. An acceleration system for charged nuclear particles with mass number equal or greater than 1, comprising:
a rotating mechanical gantry structure;
at least one radiofrequency (RF) linear accelerator configured for producing a pulsed ion beam,
said accelerator comprising at least one linac section mounted on the rotating gantry structure, the accelerator configured for rotating around an axis to irradiate a target or patient from more than one direction with the produced pulsed ion beam, the produced pulsed ion beam configured for treating a patient tumor or malformation; and
radio-frequency (RF) power generators located outside the rotating gantry structure and connected to the at least one linac section via rotating wave-guide devices.

2. A system for ion acceleration according to claim 1, further comprising:
an ion source producing an ion beam; and
a particle accelerator, configured as pre-accelerator to impart energy to particles within the ion beam, produced by the ion source, before injecting the ion beam into the at least one linac section mounted on the rotating gantry structure.

3. A system for ion acceleration according to claim 2, wherein the pre-accelerator is another linac section.

4. A system for ion acceleration according to claim 2, wherein the pre-accelerator is a cyclotron.

5. A system for ion acceleration according to claim 1, a system for ion beam delivery mounted on the rotating gantry structure.

6. A system for ion acceleration according to claim 1, wherein,
the at least one linac section comprises plural linac sections, and
each linac section is configured to run at a different frequency.

7. A system for ion acceleration according to claim 1, wherein,
the linac section comprises plural successive accelerating modules mounted on the rotating gantry structure, and
output energy of the pulsed ion beam is modulated by varying an input (RF) power to each of the successive accelerating modules which constitute the linac section.

8. A system for ion acceleration according to claim 1, wherein the pulsed ion beam is made of protons.

9. A system for ion acceleration according to claim 8, wherein the pulsed ion beam further is made of carbon ions.

10. A system for ion acceleration according to claim 1, wherein the pulsed ion beam comprises 230 MeV protons.

11. A method of producing radiopharmaceuticals, comprising a step of producing a pulsed ion beam using the system of claim 1.

12. A method of providing cancer radiation therapy, comprising the step of producing a pulsed ion beam using the system of claim 1.

13. An acceleration system for charged nuclear particles with mass number equal or greater than 1, comprising:
a rotating mechanical gantry structure;
at least one radiofrequency (RF) linear accelerator configured for producing a pulsed ion beam,
said accelerator comprising at least one linac section mounted on the rotating gantry structure, the accelerator configured for rotating around an axis to irradiate a target or patient from more than one direction with the produced pulsed ion beam, the produced pulsed ion beam configured for treating a patient tumor or malformation;
an ion source configured to produce an ion beam; and
a particle accelerator, configured as pre-accelerator to impart energy to particles within the ion beam, produced by the ion source, before injecting the ion beam into the linac section mounted on the rotating gantry structure, wherein at least one of i) the ion source and ii) the pre-accelerator are mounted on the rotating gantry structure.

14. A system for ion acceleration according to claim 13, further comprising radio-frequency (RF) power generators mounted on the rotating gantry structure and directly connected to the at least one linac section.

15. An acceleration system for charged nuclear particles with mass number equal or greater than 1, comprising:
   a rotating mechanical structure rotating around an axis; and
   at least one radiofrequency (RF) linear accelerator configured to produce a pulse ion beam,
   said at least one radiofrequency (RF) linear accelerator comprising at least one linac section mounted on the rotating mechanical structure, the accelerator configured to irradiate a target or patient from more than one direction with the produced pulsed ion beam, the produced ion beam configured for treating a patient tumor or malformation; and
   a particle accelerator, configured as pre-accelerator and arranged to impart energy to particles within an ion beam before injecting the ion beam into the linac section, wherein the the pre-accelerator is one of i) a cyclotron, and ii) a Fixed Field Alternating Gradient(FFAG) accelerator.

16. A system for ion acceleration according to claim 15, wherein the pre-accelerator is a cyclotron.

17. A system for ion acceleration according to claim 15, wherein the pre-accelerator is a FFAG accelerator.

* * * * *

UNITED STATES PATENT AND TRADEMARK OFFICE
CERTIFICATE OF CORRECTION

PATENT NO.         : 8,405,056 B2  
APPLICATION NO.    : 12/521724  
DATED              : March 26, 2013  
INVENTOR(S)        : Amaldi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 759 days.

Signed and Sealed this
First Day of September, 2015

Michelle K. Lee
*Director of the United States Patent and Trademark Office*